(12) United States Patent
Hsu

(10) Patent No.: US 9,247,637 B2
(45) Date of Patent: Jan. 26, 2016

(54) STRAIN RELIEF STRUCTURES FOR STRETCHABLE INTERCONNECTS

(71) Applicant: MC10, Inc., Cambridge, MA (US)

(72) Inventor: Yung-Yu Hsu, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 419 days.

(21) Appl. No.: 13/843,880

(22) Filed: Mar. 15, 2013

(65) Prior Publication Data

US 2014/0022746 A1    Jan. 23, 2014

Related U.S. Application Data

(60) Provisional application No. 61/658,140, filed on Jun. 11, 2012, provisional application No. 61/768,939, filed on Feb. 25, 2013.

(51) Int. Cl.
*H05K 1/02*        (2006.01)

(52) U.S. Cl.
CPC ............ *H05K 1/0271* (2013.01); *H05K 1/0283* (2013.01); *A61B 2562/164* (2013.01); *A61B 2562/166* (2013.01); *A61B 2562/225* (2013.01)

(58) Field of Classification Search
CPC ............ H05K 2201/1028; H05K 2201/10287; H05K 1/0393; H05K 1/189; H05K 1/118
USPC ......... 361/748, 749, 750, 751, 760, 761, 762, 361/764, 765, 776, 783; 174/521, 251, 254, 174/255, 256

See application file for complete search history.

(56) References Cited

U.S. PATENT DOCUMENTS

| | | | |
|---|---|---|---|
| 7,265,298 B2 | 9/2007 | Maghribi | |
| 7,337,012 B2 | 2/2008 | Maghribi | |
| 7,487,587 B2 | 2/2009 | Vanfleteren | |
| 7,491,892 B2 | 2/2009 | Wagner | |
| 7,521,292 B2 | 4/2009 | Rogers | |

(Continued)

FOREIGN PATENT DOCUMENTS

| | | |
|---|---|---|
| WO | WO 2005/122285 A2 | 12/2005 |
| WO | WO 2008/030960 A2 | 3/2008 |

(Continued)

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

(Continued)

*Primary Examiner* — Jenny L Wagner
*Assistant Examiner* — Ahmad D Barnes
(74) *Attorney, Agent, or Firm* — Nixon Peabody LLP

(57) ABSTRACT

Intersection structures are provided to reduce a strain in a conformable electronic system that includes multi-level arrangements of stretchable interconnect structures. Bypass regions are formed in areas of the stretchable interconnect structures that may ordinarily cross or pass each other. The bypass regions of the stretchable interconnects are disposed relative to each other such that the intersection structure encompasses at least a portion of the bypass regions of each stretchable interconnect structure. The intersection structure has elastic properties that relieve a mechanical strain on the bypass regions during stretching at least one of the stretchable interconnect structures.

30 Claims, 14 Drawing Sheets

(56) References Cited

U.S. PATENT DOCUMENTS

| | | |
|---|---|---|
| 7,557,367 B2 | 7/2009 | Rodgers |
| 7,622,367 B1 | 11/2009 | Nuzzo |
| 7,759,167 B2 | 7/2010 | Vanfleteren |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rodgers |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rodgers |
| 8,664,699 B2 | 3/2014 | Nuzzo |
| 8,679,888 B2 | 3/2014 | Rodgers |
| 8,729,524 B2 | 5/2014 | Rodgers |
| 8,754,396 B2 | 6/2014 | Rogers |
| 8,865,489 B2 | 10/2014 | Rodgers |
| 8,886,334 B2 | 11/2014 | Ghaffari |
| 8,905,772 B2 | 12/2014 | Rodgers |
| 2002/0094701 A1 | 7/2002 | Biegelsen |
| 2003/0214408 A1 | 11/2003 | Grajales |
| 2004/0192082 A1* | 9/2004 | Wagner et al. ............... 439/67 |
| 2004/0243204 A1 | 12/2004 | Maghribi |
| 2006/0038182 A1 | 2/2006 | Rodgers |
| 2006/0286785 A1 | 12/2006 | Rogers |
| 2008/0046080 A1 | 2/2008 | Vanden Bulcke |
| 2008/0157235 A1 | 7/2008 | Rodgers |
| 2008/0204021 A1 | 8/2008 | Leussler |
| 2008/0257589 A1* | 10/2008 | Ostmann et al. ............ 174/254 |
| 2009/0107704 A1 | 4/2009 | Vanfleteren |
| 2009/0261828 A1 | 10/2009 | Nordmeyer-Massner |
| 2009/0294803 A1 | 12/2009 | Nuzzo |
| 2010/0002402 A1 | 1/2010 | Rodgers |
| 2010/0059863 A1 | 3/2010 | Rogers |
| 2010/0072577 A1 | 3/2010 | Nuzzo |
| 2010/0087782 A1 | 4/2010 | Ghaffari |
| 2010/0116526 A1 | 5/2010 | Arora |
| 2010/0178722 A1 | 7/2010 | De Graff |
| 2010/0271191 A1 | 10/2010 | De Graff |
| 2010/0298895 A1 | 11/2010 | Ghaffari |
| 2010/0317132 A1 | 12/2010 | Rodgers |
| 2010/0321161 A1 | 12/2010 | Isabell |
| 2011/0034912 A1 | 2/2011 | De Graff |
| 2011/0054583 A1 | 3/2011 | Litt |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0277813 A1 | 11/2011 | Rodgers |
| 2012/0051005 A1 | 3/2012 | Vanfleteren |
| 2012/0052268 A1 | 3/2012 | Axisa |
| 2012/0065937 A1 | 3/2012 | De Graff |
| 2012/0092178 A1 | 4/2012 | Callsen |
| 2012/0106095 A1 | 5/2012 | Daniel |
| 2012/0157804 A1 | 6/2012 | Rodgers |
| 2012/0172697 A1 | 7/2012 | Urman |
| 2012/0226130 A1 | 9/2012 | De Graff |
| 2012/0244848 A1 | 9/2012 | Ghaffari |
| 2012/0256308 A1 | 10/2012 | Helin |
| 2012/0327608 A1 | 12/2012 | Rodgers |
| 2013/0041235 A1 | 2/2013 | Rodgers |
| 2013/0099358 A1 | 4/2013 | Elolampi |
| 2013/0100618 A1 | 4/2013 | Rogers |
| 2013/0118255 A1 | 5/2013 | Callsen |
| 2013/0150693 A1 | 6/2013 | D'angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0225965 A1 | 8/2013 | Ghaffari |
| 2013/0245388 A1 | 9/2013 | Rafferty |
| 2013/0274562 A1 | 10/2013 | Ghaffari |
| 2013/0313713 A1 | 11/2013 | Arora |
| 2013/0316487 A1 | 11/2013 | De Graff |
| 2013/0320503 A1 | 12/2013 | Nuzzo |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0104793 A1 | 4/2014 | Park |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora |

FOREIGN PATENT DOCUMENTS

| | | |
|---|---|---|
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/049716 A1 | 4/2013 |
| WO | WO 2013/052919 A2 | 4/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |

OTHER PUBLICATIONS

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

(56) References Cited

OTHER PUBLICATIONS

Kim et al., "Stretchable and Foldable Silicon Integrated Circuits," Science, vol. 320, 507-511 (5 pages) (Apr. 25, 2008).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Kim et al.: 'Stretchable Electronics: Materials Strategies and Devices.' Advanced Materials vol. 20, no. Issue, Dec. 17, 2008, pp. 4887-4892.

International Search Report, Application No. PCT/US14/017975, date of mailing Jun. 23, 2014, 2 pages.

* cited by examiner

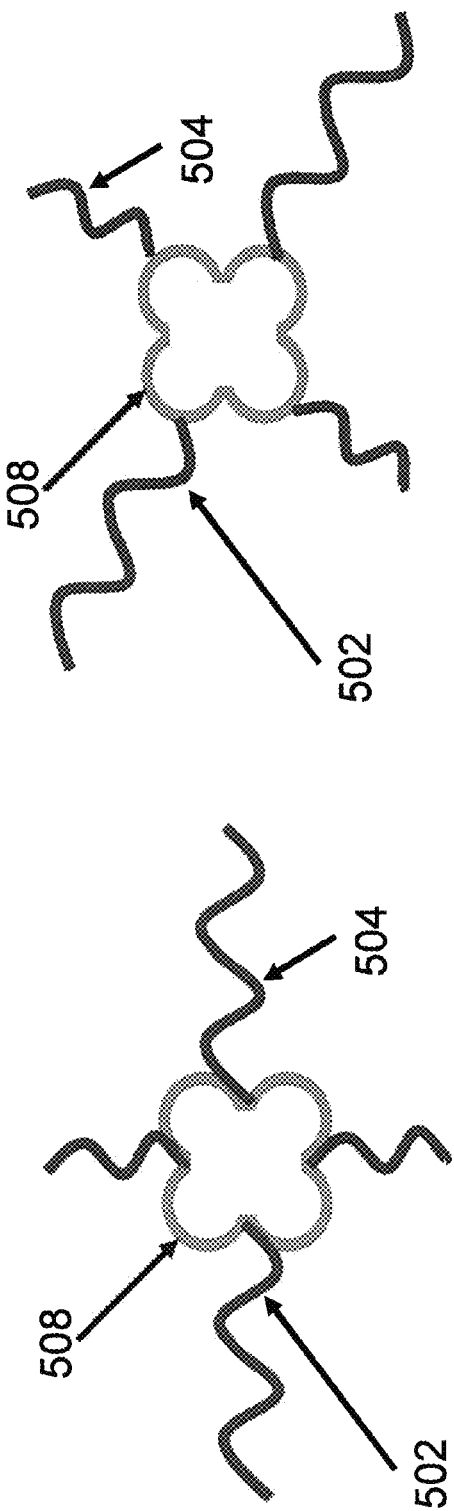
FIG. 5A
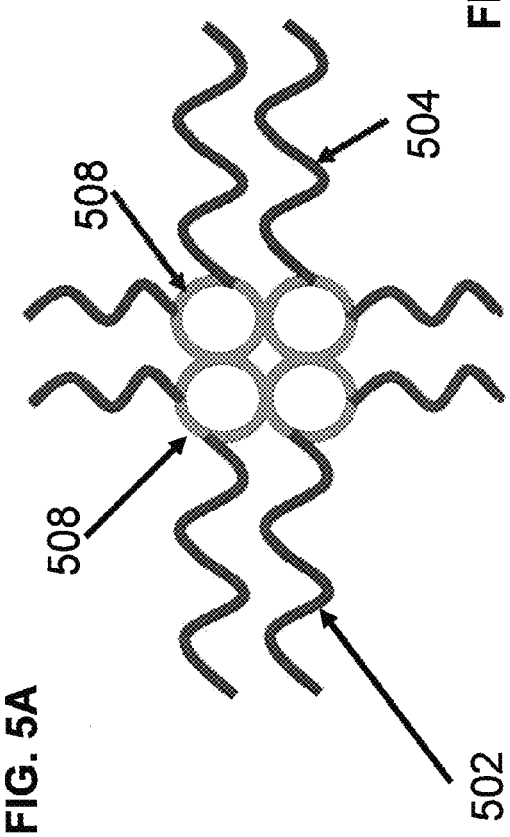
FIG. 5B
FIG. 5C

STRAIN RELIEF STRUCTURES FOR STRETCHABLE INTERCONNECTS

CROSS-REFERENCE TO RELATED APPLICATIONS

This application claims priority to and benefit of United States Provisional Application No. 61/658,140, filed on Jun. 11, 2012, entitled "STRAIN RELIEF STRUCTURES," and U. S. Provisional Application No. 61/768,939, filed on Feb. 25, 2013, entitled "MULTI-LAYER THIN FILM STRETCHABLE INTERCONNECTS," which provisional applications are incorporated herein by reference in their entirety, including drawings.

BACKGROUND

High quality medical sensing and imaging data has become increasingly beneficial in the diagnoses and treatment of a variety of medical conditions. The conditions can be associated with the digestive system, the cardio-circulatory system, and can include injuries to the nervous system, cancer, and the like. To date, most electronic systems that could be used to gather such sensing or imaging data have been rigid and inflexible. These rigid electronics are not ideal for many applications, such as in biomedical devices. Most of biological tissue is soft and curved. The skin and organs are delicate and far from two-dimensional.

Other potential applications of electronics systems, such as for gathering data in non-medical systems, also can be hampered by rigid electronics.

SUMMARY

The Inventors have recognized that the inflexibility of electronic systems in use are not ideal for many applications.

In view of the foregoing, various examples described herein are directed generally to systems, apparatus and methods for providing strain relief in a conformable electronic system. The systems, methods and apparatus described herein provide effective, compact, and complex systems that include stretchable interconnects disposed in multiple layers.

In an example, a closed-form strain relief (intersection) structure is described that effectively redistributes the strain that might normally act on regions of crossing or close passage of stretchable interconnects.

In an example, a system, apparatus and method is provided that is based on thin device islands, including integrated circuitry (IC) chips and/or stretchable interconnects that are embedded in a flexible polymer.

An example apparatus is provided that includes a first conductive stretchable interconnect comprising a first bypass region, a second conductive stretchable interconnect comprising a second bypass region, and an intersection structure. The second conductive stretchable interconnect is disposed in relation to the first conductive stretchable interconnect such that the intersection structure encompasses at least a portion of the first bypass region and the second bypass region, and the intersection structure has elastic properties that relieve a mechanical strain on the first bypass region and the second bypass region during stretching of the first conductive stretchable interconnect and/or the second conductive stretchable interconnect.

An example device is also provided that includes a flexible substrate, at least two device components disposed over the flexible substrate, a first conductive stretchable interconnect in electrical communication with at least one of the at least two device components, the first conductive stretchable interconnect comprising a first bypass region, a second conductive stretchable interconnect in electrical communication with at least one other of the at least two device components, the second conductive stretchable interconnect comprising a second bypass region, and an intersection structure. The second conductive stretchable interconnect is disposed in relation to the first conductive stretchable interconnect such that the intersection structure encompasses at least a portion of the first bypass region and the second bypass region. The intersection structure has elastic properties that relieve a mechanical strain on the first bypass region and the second bypass region during stretching of the first conductive stretchable interconnect and/or the second conductive stretchable interconnect.

In an example, at least one of the at least two device components can include an electronic device, an optical device, an opto-electronic device, a mechanical device, a microelectromechanical device, a nanoelectromechanical device, a microfluidic device and a thermal device.

The following publications, patents, and patent applications are hereby incorporated herein by reference in their entirety:

Kim et al., "Stretchable and Foldable Silicon Integrated Circuits," Science Express, Mar. 27, 2008, 10.1126/science.1154367;

Ko et al., "A Hemispherical Electronic Eye Camera Based on Compressible Silicon Optoelectronics," Nature, Aug. 7, 2008, vol. 454, pp. 748-753;

Kim et al., "Complementary Metal Oxide Silicon Integrated Circuits Incorporating Monolithically Integrated Stretchable Wavy Interconnects," Applied Physics Letters, Jul. 31, 2008, vol. 93, 044102;

Kim et al., "Materials and Noncoplanar Mesh Designs for Integrated Circuits with Linear Elastic Responses to Extreme Mechanical Deformations," PNAS, Dec. 2, 2008, vol. 105, no. 48, pp. 18675-18680;

Meitl et al., "Transfer Printing by Kinetic Control of Adhesion to an Elastomeric Stamp," Nature Materials, January, 2006, vol. 5, pp. 33-38;

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;" and U.S. Patent Application publication no. 2010 027119-A1, published Oct. 28, 2010, filed Nov. 24, 2009, and entitled "SYSTEMS, DEVICES, AND METHODS UTILIZING STRETCHABLE ELECTRONICS TO MEASURE TIRE OR ROAD SURFACE CONDITIONS."

Kim, D. H. et al. (2010). Dissolvable films of silk fibroin for ultrathin conformal biointegrated electronics. *Nature Materials*, 9, 511-517.

Omenetto, F. G. and D. L. Kaplan. (2008). A new route for silk. *Nature Photonics*, 2, 641-643.

Omenetto, F. G., Kaplan, D. L. (2010). New opportunities for an ancient material. *Science*, 329, 528-531.

Halsed, W. S. (1913). Ligature and suture material. *Journal of the American Medical Association*, 60, 1119-1126.

Masuhiro, T., Yoko, G., Masaobu, N., et al. (1994). Structural changes of silk fibroin membranes induced by immersion in methanol aqueous solutions. *Journal of Polymer Science*, 5, 961-968.

Lawrence, B. D., Cronin-Golomb, M., Georgakoudi, I., et al. (2008). Bioactive silk protein biomaterial systems for optical devices. *Biomacromolecules*, 9, 1214-1220.

Demura, M., Asakura, T. (1989). Immobilization of glucose oxidase with *Bombyx mori* silk fibroin by only stretching treatment and its application to glucose sensor. *Biotechnololgy and Bioengineering*, 33, 598-603.

Wang, X., Zhang, X., Castellot, J. et al. (2008).Controlled release from multilayer silk biomaterial coatings to modulate vascular cell responses. *Biomaterials*, 29, 894-903.

U.S. patent application Ser. No. 12/723,475 entitled "SYSTEMS, METHODS, AND DEVICES FOR SENSING AND TREATMENT HAVING STRETCHABLE INTEGRATED CIRCUITRY," filed Mar. 12, 2010.

U.S. patent application Ser. No. 12/686,076 entitled "Methods and Applications of Non-Planar Imaging Arrays," filed Jan. 12, 2010.

U.S. patent application Ser. No. 12/636,071 entitled "Systems, Methods, and Devices Using Stretchable or Flexible Electronics for Medical Applications," filed Dec. 11, 2009.

U.S. Patent Application publication no 2012-0065937-A1, published Mar. 15, 2012, and entitled "METHODS AND APPARATUS FOR MEASURING TECHNICAL PARAMETERS OF EQUIPMENT, TOOLS AND COMPONENTS VIA CONFORMAL ELECTRONICS."

U.S. patent application Ser. No. 12/616,922 entitled "Extremely Stretchable Electronics," filed Nov. 12, 2009.

U.S. patent application Ser. No. 12/575,008 entitled "Catheter Balloon Having Stretchable Integrated Circuitry and Sensor Array," filed on Oct. 7, 2009.

U.S. patent application Ser. No. 13/336,518 entitled "Systems, Methods, and Devices Having Stretchable Integrated Circuitry for Sensing and Delivering Therapy," filed Dec. 23, 2011.

It should be appreciated that all combinations of the foregoing concepts and additional concepts described in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the figures, described herein, are for illustration purposes only, and that the drawings are not intended to limit the scope of the disclosed teachings in any way. In some instances, various aspects or features may be shown exaggerated or enlarged to facilitate an understanding of the inventive concepts disclosed herein (the drawings are not necessarily to scale, emphasis instead being placed upon illustrating the principles of the teachings). In the drawings, like reference characters generally refer to like features, functionally similar and/or structurally similar elements throughout the various figures.

FIGS. 5A-5C show example configurations of intersection structures, according to the principles described herein.

DETAILED DESCRIPTION

Figure 1:
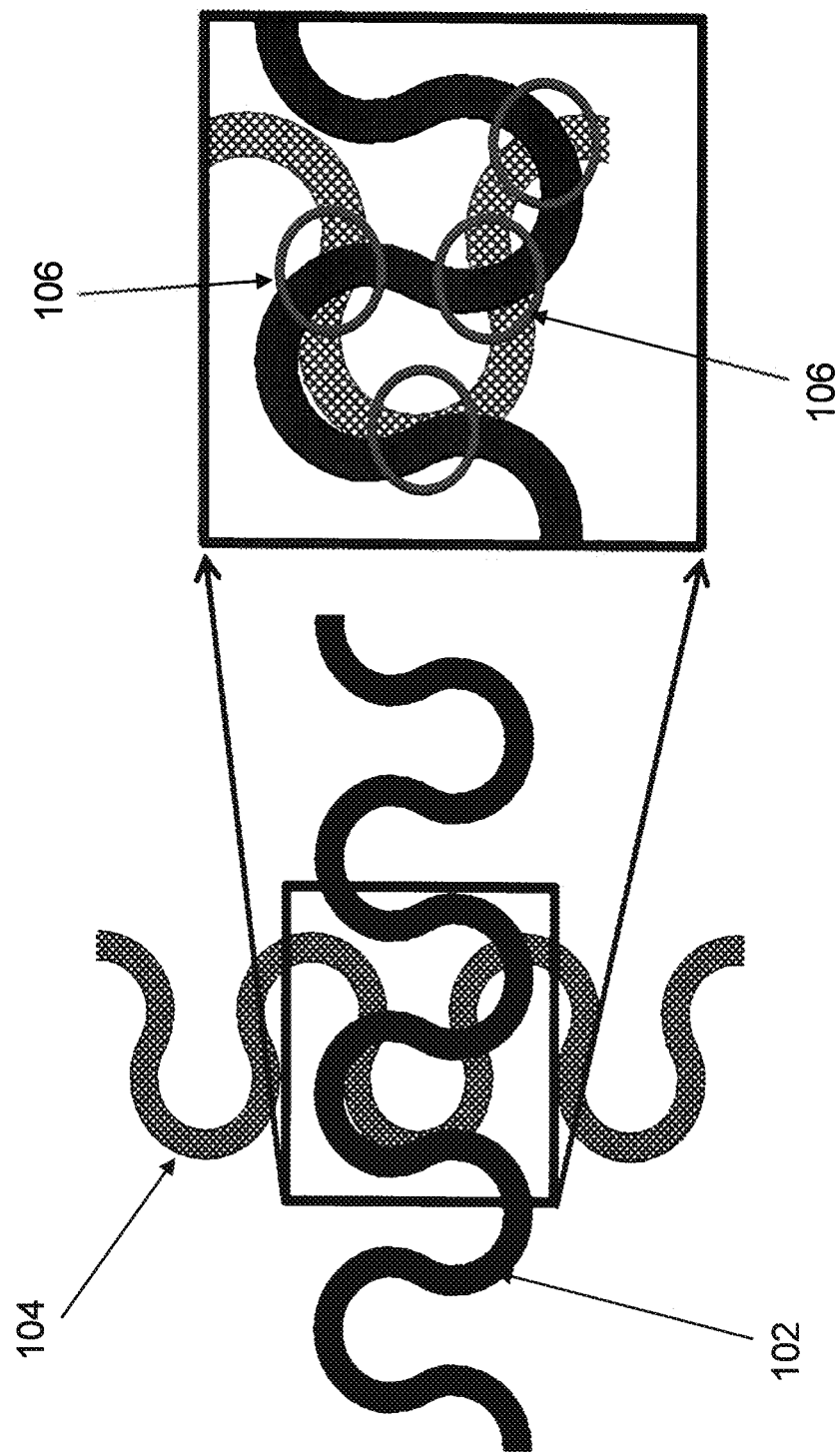
FIG. 1 shows a portion of an example electronic system that includes stretchable interconnects, according to the principles described herein.

Following below are more detailed descriptions of various concepts related to, and embodiments of, an apparatus and systems for embedding thinned chips in a flexible polymer. It should be appreciated that various concepts introduced above and described in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on. As used herein, the term "disposed on" or "disposed above" is defined to encompass "at least partially embedded in."

With respect to substrates or other surfaces described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a substrate or a layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the substrate (or other surface) and each other. The terms "disposed on" "disposed in" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

A system, apparatus and method described herein provides strain relief in a conformable electronic system. In order to create effective, compact, and complex systems, the stretchable interconnects according to the principles described herein are designed to overlap one another in multiple layers. The strain relief (intersection) structure according to the principles described herein can b implemented to effectively redistributes the strain that can act stretchable interconnects in a device structure.

An example system, apparatus and method described herein provides strain relief in a conformable electronic system such that the system can be stretched to elongations of up to about 20%, about 50%, about 70%, about 80%, or more of an original dimension of the stretchable interconnects, without formation of micro-cracks in the stretchable interconnects.

Another example system, apparatus and method described herein provides strain relief in a conformable electronic system such that the system can be stretched to elongations of up to about 100%, about 120%, about 150%, about 150%, about 180%, about 200%, about 250%, about 280% or more of an original dimension of the stretchable interconnects, without detachment, rupture, or other mechanical failure of the stretchable interconnects.

The electronic systems described herein are capable of bending, twisting, and stretching, and have great potential for applications in which conventional, stiff semiconductor microelectronics present limitations. The conformable electronics described herein have numerous applications, including but not limited to human body sweat monitors, stretchable solar panels, and cardiac catheters. For example, the conformable electronics described herein can be applied in interventional balloon catheters for cardiac ablation, implantable devices, and wearable electronic systems.

The example electronic devices according to the principles described herein can include electrodes, sensors, active devices, and/or metal wires for connecting or transmitting electrical signals. Some of these components may be inflexible. The stretchable interconnects that include the strain relief (intersection) structures according to the principles described herein can be used to provide a degree of flexibility or deformability to the electronic devices. The example electronic devices include both rigid and bendable elements, including thin electronic chips coupled through stretchable interconnects. The stretchable interconnects that include the strain relief (intersection) structures according to the principles described herein are configured to withstand the majority of the deformations applied to the system, while maintaining electrical performance as well as structural integrity.

The example systems, methods and apparatus described herein are applicable to stretchable interconnects of a non-coplanar stretchable interconnect configuration or an in-plane stretchable interconnect configuration. Non-limiting examples of non-coplanar stretchable interconnect structures include buckled interconnects. Non-limiting examples of in-plane stretchable interconnects include horseshoe-patterned meandering interconnects, serpentine interconnects, rippled interconnects, and zig-zag interconnects. In an example, to form the noncoplanar stretchable interconnect structures, a conductive material can be deposited onto a pre-stretched elastomeric substrate and allowed to relax. In an example, to form the in-plane stretchable interconnect structures, the conductive material can be deposited on a relaxed substrate and patterned to the desired configuration.

The example systems, methods and apparatus described herein provide conformable electronic systems with a greater degree of complexity, smaller form factors, and more sensing modalities. The stretchable multi-layered metal interconnects according to the principles described herein are configured to mitigate the increased strain that can occur in a multi-layer system. The multi-layer in-plane patterned stretchable interconnects can be fabricated through bottom-up micro-fabrication process.

FIG. 1 shows a portion of an example electronic system that includes horse-shoe shaped stretchable interconnects 102 and 104 disposed in at least two layers of a multi-layer system, with the horseshoe-patterned meandering portions overlapping one another. Where the multiple meandering interconnects intersect, such as at the junctions 106 in FIG. 1, the interconnects can experience mechanical constraints subject to the specific orientation of each stretchable interconnects 102, 104. The incidence of constraints at junctions 106 between stretchable interconnects in neighboring layers can adversely affect the fabrication process at these small junction areas and can result in undesirable mechanics effects during stretching of the ultimate conformable electronic system.

Figure 2A:
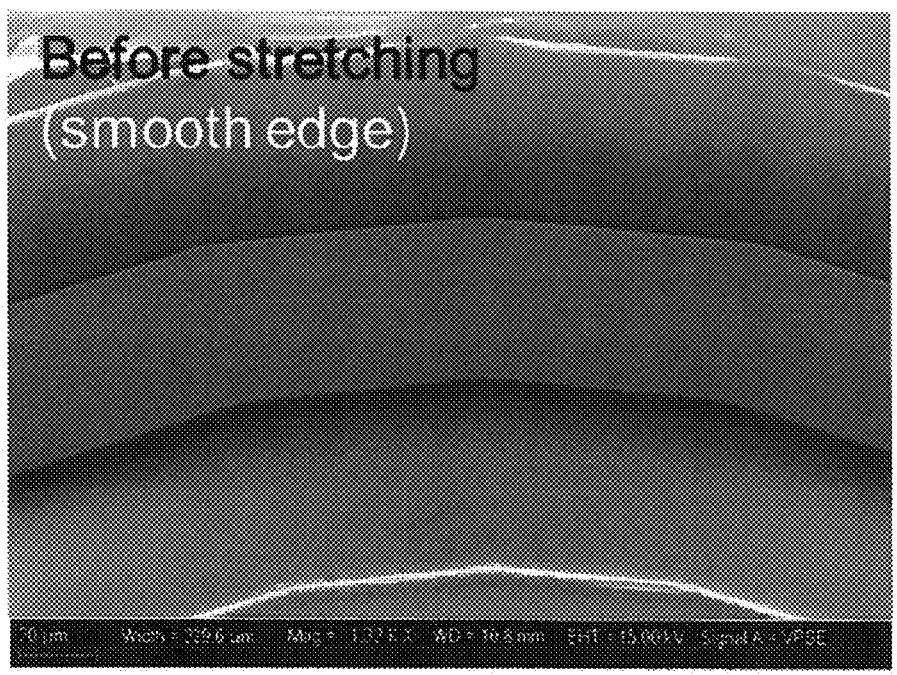
FIGS. 2A-2B show SEM images of an example stretchable interconnect (2A) prior to stretching and (2B)after stretching, according to the principles described herein.
Figure 2B:
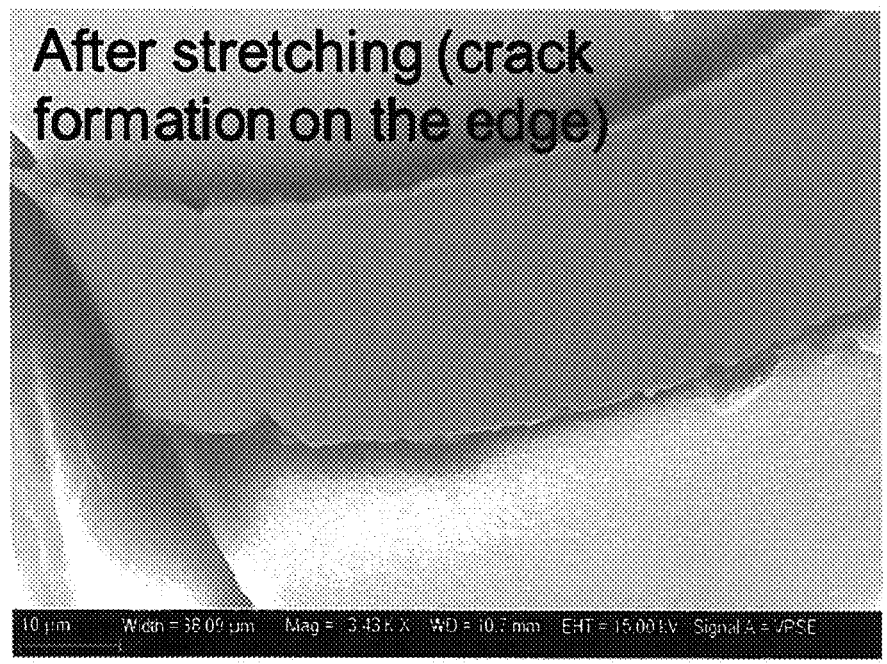

FIGS. 2A and 2B show scanning electron microscope (SEM) images of a portion of a horseshoe-shaped stretchable interconnect at the crest of a "horse-shoe." FIG. 2A shows a SEM image of the stretchable interconnect prior to stretching. FIG. 2B shows a SEM image of the stretchable interconnect after stretching that results in formation of micro-cracks. The non-limiting example stretchable interconnects are formed from gold (Au). As shown in FIG. 2A, the edge of the Au layer is smooth and free of damage or other defect. FIG. 2B shows the kind of failure that can begin to occur in a stretchable interconnect, with the formation of micro-crack. The edge of the Au layer is rough with indentations, and micro-cracks extending into the Au layer are visible. These micro-cracks as well as the edge roughness in the Au layer can decrease the contiguous cross-sectional area of the interconnect as it is stretched, causing the electrical resistance of the structure to increase. The change in electrical resistance as a result of micro-crack formation in the stretchable interconnect can adversely affect the performance of an electronic device.

The example systems, methods and apparatus according to the principles described herein provide novel strain relief (intersection) structures and configurations for the stretchable interconnects that can be implemented to relieve the strain that can occur at the junctions between multiple metal interconnect layers. The strain relief (intersection) structure and novel configurations for the stretchable interconnects according to the principles described herein can be implemented in any number of systems with multiple interconnecting layers of interconnects.

The example systems, methods and apparatus according to the principles described herein provide novel strain relief (intersection) structures and configurations for the stretchable interconnects that can be implemented to relieve plastic strain in overlapping stretchable electronic interconnects. The novel strain relief (intersection) structures and configurations for the stretchable interconnects can be implemented to effectively redistribute strain from the junctions of the interconnects. The example systems, methods and apparatus according to the principles described herein provide multi-layer strain relief (intersection) structures for stretchable electronic systems that are durable and can improve the performance of conformable electronic devices.

To relieve strain at the intersection region and to reduce the complexity of the design of the intersection region, a strain relief (intersection) structure having a curved conformation is described herein. The multiple layers of patterned stretchable interconnects can be disposed to perpendicularly cross one another, and intersect at the intersection structure (that provides strain relief). An intersection region having a curved conformation has the ability to acts as an elastic spring as the electronic device structure is stretched.

Figure 3A:
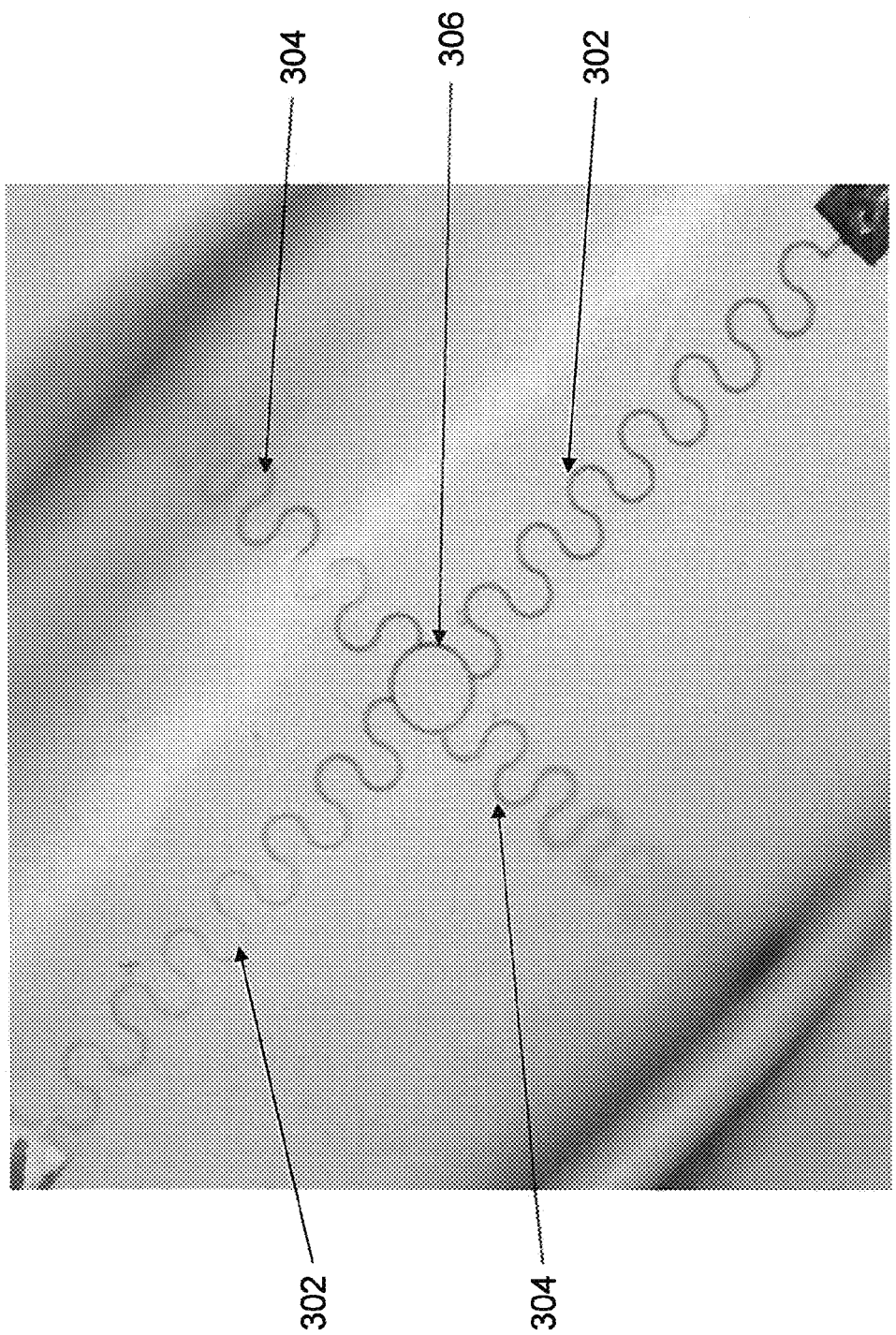
FIG. 3A shows an example apparatus that includes a strain relief structure, according to the principles described herein.

FIG. 3A shows a non-limiting example apparatus that includes a strain relief (intersection) structure and configuration of the stretchable interconnects disposed on a flexible substrate, according to the principles described herein. The example apparatus includes stretchable interconnects 302 and 304 that cross each other at a portion of the apparatus. According to the principles described herein, each stretchable interconnect 302 and 304 is fabricated to include a bypass region 306. In the non-limiting example of FIG. 3A, the bypass region of each stretchable interconnect is formed as a substantially circular curve that runs across the junction of the two stretchable interconnects. As shown in the example of FIG. 3A, the stretchable interconnect 302 and 304 are positioned in the apparatus such that the bypass region of one of the stretchable interconnects is proximate to the bypass region of the other stretchable interconnect. The strain relief (intersection) structure (intersection structure) is positioned at the area of the bypass regions 306.

Figure 3B:
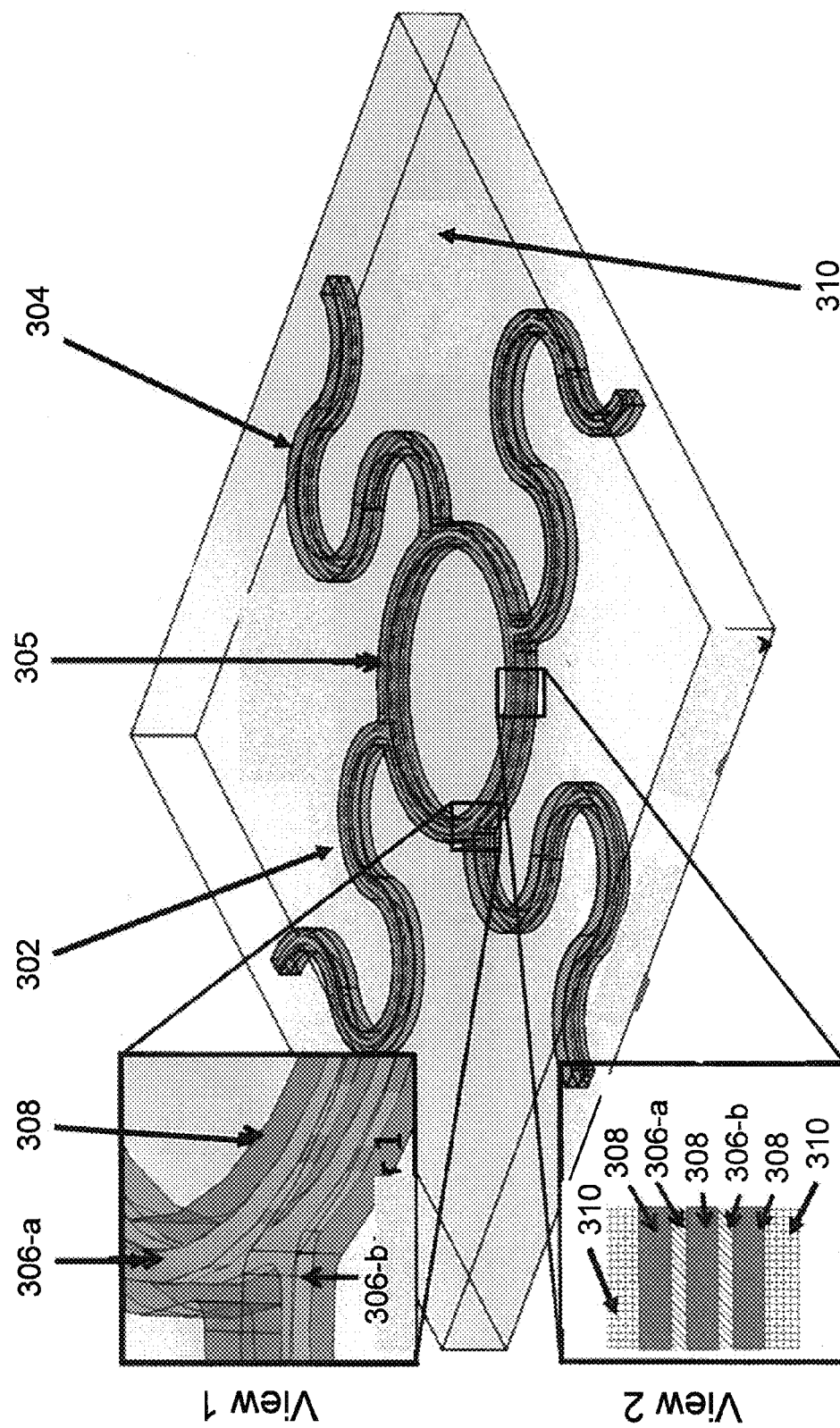
FIG. 3B shows views of an example apparatus, according to the principles described herein.

FIG. 3B shows a detailed view of the structure of the example apparatus of FIG. 3A. FIG. 3B shows the stretchable interconnects 302 and 304 entering an intersection region 305. As shown in the expanded portion of the intersection region 305 (see View 1), each of the stretchable interconnects 302 and 304 is formed with a bypass region 306-a and 306-b. In this example, bypass region 306-a is disposed above bypass region 306-b. As also shown in FIG. 3B, the junction region 305 includes an intersection structure 308. The stretchable interconnect 302 is disposed relative to the stretchable interconnect 304 such that the intersection structure 308 encompasses at least a portion of the bypass regions 306-a of one of the stretchable interconnects and the bypass region 306-b. According to the principles described herein, the intersection structure has elastic properties that relieve a mechanical strain on the bypass regions during stretching of at least one of the stretchable interconnects.

FIG. 3B shows a cross-sectional view (View 2) of the layering structure of a portion of the intersection region 305. The cross-sectional view shows portions of the bypass regions 306-a and 306-b and portions of the intersection structure 308. As shown in the non-limiting example in View 2, the intersection structure 308 can encompass the bypass regions 306-a and 306-b.

The stretchable interconnects 302 and 304 and their respective bypass regions 306-a and 306-b are formed from a conductive material. In any of the examples described herein, the conductive material can be but is not limited to a metal, a metal alloy, a conductive polymer, or other conductive material. In an example, the metal or metal alloy of the coating may include but is not limited to aluminum, stainless steel, or a transition metal (including copper, silver, gold, platinum, zinc, nickel, titanium, chromium, or palladium, or any combination thereof) and any applicable metal alloy, including alloys with carbon. In other non-limiting example, suitable conductive materials may include a semiconductor-based conductive material, including a silicon-based conductive material, indium tin oxide or other transparent conductive oxide, or Group III-IV conductor (including GaAs). The semiconductor-based conductive material can be doped.

The intersection structure can be formed from any material having elastic properties that relieve a mechanical strain on the bypass regions during stretching of at least one of the stretchable interconnects. For example, the intersection structure can be formed from a polymer or polymeric material. Non-limiting examples of applicable polymers or polymeric materials include, but are not limited to, a polyimide, a polyethylene terephthalate (PET), a silicone, or a polyeurethane. Other non-limiting examples of applicable polymers or polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer or polymeric material herein can be a UV curable polymer.

As shown in FIG. 3B, the example apparatus can be encapsulated in an encapsulant 310. The encapsulant can be formed from any of the polymer or polymeric materials described in connection with the intersection structure. In various examples, the intersection structure 308 and the encapsulant 310 can be formed from the same polymer or polymeric material, or from different polymers or polymeric materials. In an example, the encapsulant can be a silicone such as but not limited to ECOFLEX® (BASF, Florham Park, N.J.).

For applications in biomedical devices, the encapsulant should be biocompatible. The stretchable interconnect can be embedded in a polyimide that also acts as a mechanical reinforcement. The strain relief intersection structure and the stretchable interconnects can also be encapsulated by a flexible elastomeric substrate.

FIG. 3B also shows that the stretchable interconnects of the example apparatus can be encapsulated. The stretchable interconnects can be encapsulated in any of the polymer or polymeric materials described in connection with the intersection structure and the encapsulant 310. In various examples, the intersection structure 308, the encapsulant 310 can be formed from the same polymer or polymeric material, or from different combinations of polymers or polymeric materials. In an example, the stretchable interconnects can be encapsulated using a polyimide. in another example, the intersection structure 308 and the encapsulating material for the stretchable interconnects can be formed from the same material. As a result, the encapsulating material for the stretchable interconnects and the intersection structure can be formed as a contiguous structure or as a continuous structure.

Figure 3C:
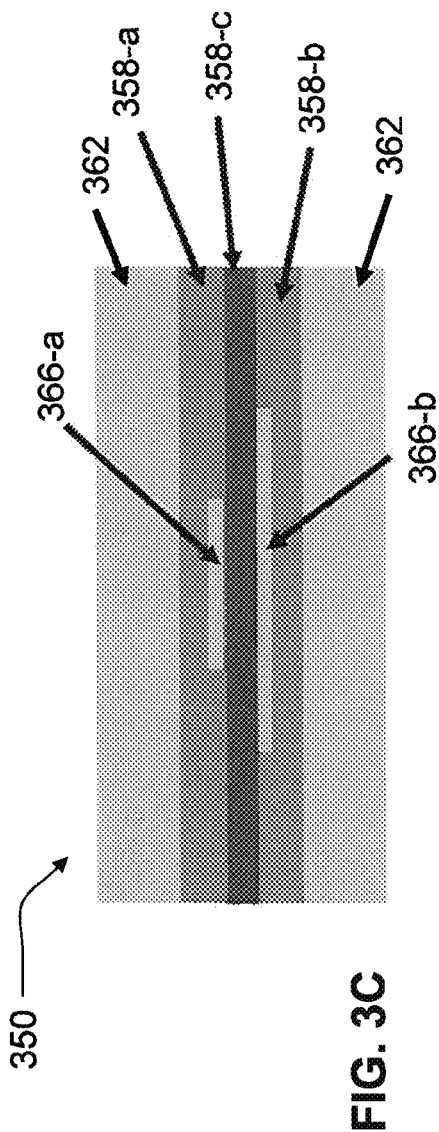
FIG. 3C show an example cross-section of an intersection region, according to the principles described herein.

FIG. 3C shows another example cross-section of a portion of an intersection region. The layering structure of the cross-section shows the bypass regions 366-a and 366-b forming a part of the stretchable interconnects and the intersection structure 358 that encompasses a portion of the bypass regions 366-a and 366-b. In this example, the intersection structure 358 includes material layers 358-a and 358-b above and below the bypass regions, and a sandwich layer 358-c positioned between the bypass regions 366-a and 366-b. The sandwich lyaer 358-c can be formed from an adhesive material. The intersection region can be encapsulated in an encapsulant 362.

In any of the example structures described herein, the bypass regions of the stretchable interconnects can have a thickness of about 0.1 µm, about 0.3 µm, about 0.5 µm, about 0.8 µm, about 1 µm, about 1.5 µm, about 2 µm or greater. The intersection structure at portions 358-a and 358-b can have a thickness of about 5 µm, about 7.5 µm, about 9 µm, about 12 µm or greater, with a sandwich layer portion 358-c having a thickness of about 1 µm, about 1.5 µm, about 2 µm, about 2.5 µm, about 3 µm or greater. FIG. 3C shows another example cross-section of a portion of an intersection region. In any example herein, the encapsulant can have a thickness of about 100 µm, about 125 µm, about 150 µm, about 175 µm, about 200 µm, about 225 µm, about 250 µm, about 300 µm or greater.

Figure 4A:
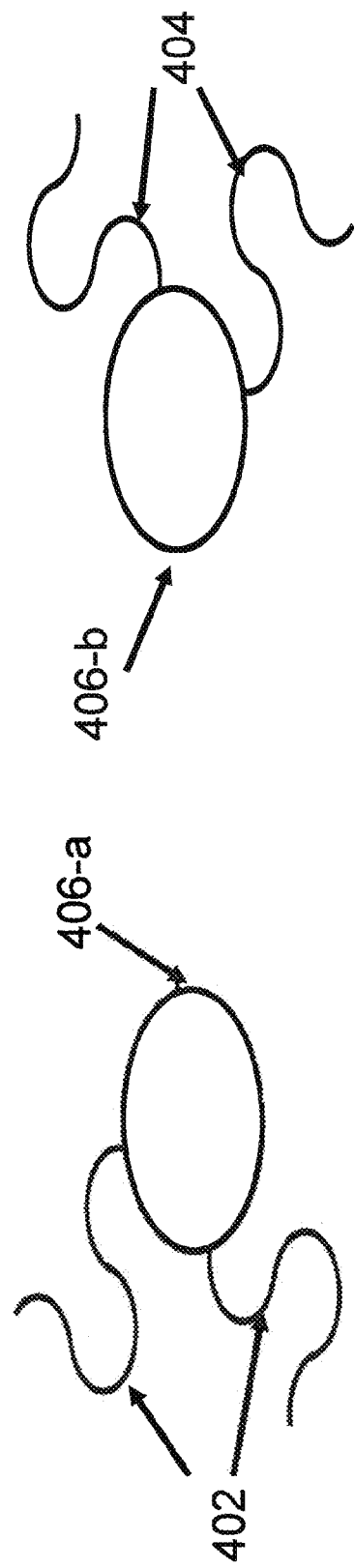
FIGS. 4A-4C show examples of stretchable interconnects that include different conformations of bypass regions, according to the principles described herein.
Figure 4B:
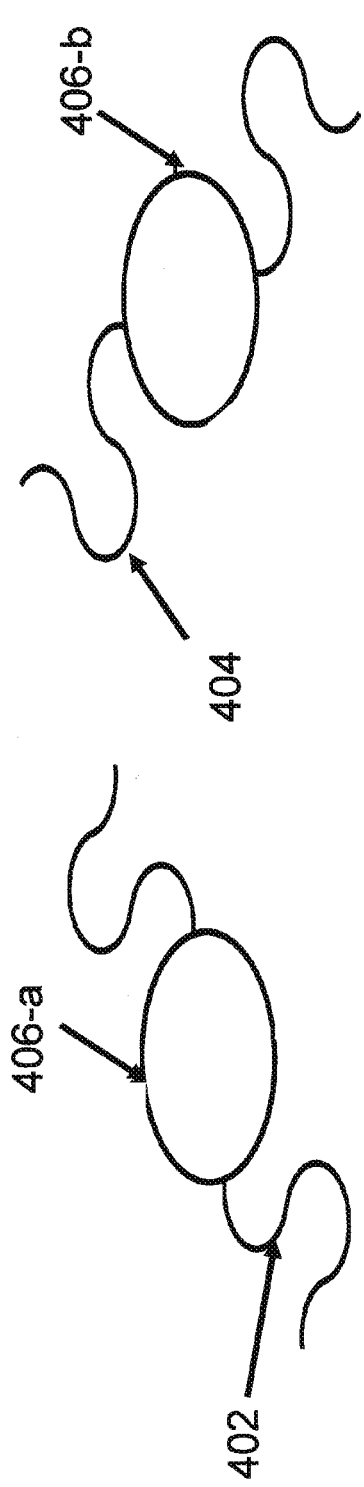
Figure 4C:
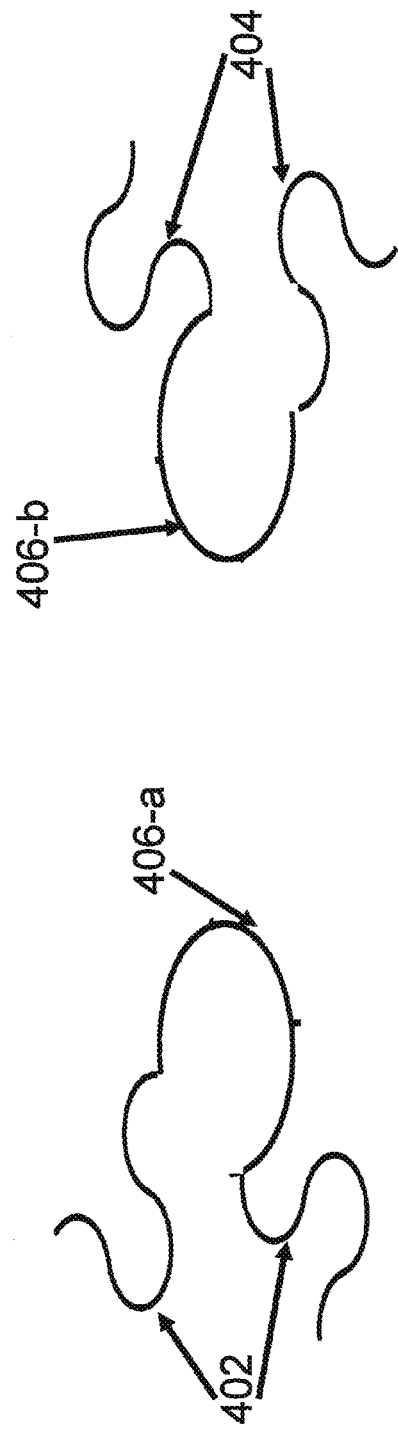

FIGS. 4A-4C show non-limiting examples of the configurations of stretchable interconnects 402, 404 and bypass regions 406-a and 406-b that can be used with an intersection structure having a substantially closed-form curve conformation. As shown in FIG. 4A, the bypass region 406-a and 406-b of each stretchable interconnect also can have a substantially closed-form curve configuration. The stretchable interconnects 402, 404 of FIG. 4A can be positioned in the example apparatus such that the bypass regions 406-a and 406-b coincide with each other, to be encompassed in an intersection structure as described herein. FIG. 4B also shows bypass region 406-a and 406-b of stretchable interconnects that have a substantially closed-form curve configuration. The stretchable interconnects 402, 404 in FIG. 4B extend from opposite sides of the bypass regions 406-a and 406-b rather than substantially the same side of the bypass regions 406-a and 406-b, as shown in FIG. 4A. In FIG. 4B as well, the stretchable interconnects 402, 404 can be positioned such that the bypass regions 406-a and 406-b coincide with each other, to be encompassed in an intersection structure as described herein. In the example of FIG. 4C, the bypass regions 406-a and 406-b are formed as open-curve structures in stretchable interconnects 402, 404. The stretchable interconnects 402, 404 of FIG. 4C also can be positioned such that the bypass regions 406-a and 406-b coincide with each other, to be encompassed in an intersection structure as described herein.

FIGS. 5A-5C show other non-limiting example configurations of intersection structures 508, and the different configurations of intersection structures 502, 504 that can be used with the intersection structures. As shown in FIGS. 5A and 5B, the intersection structure 508 can be formed as an open-curve structure, e.g., in a clover pattern. As a non-limiting example, the example intersection structure 508 of FIG. 5A or 5B can be used with stretchable interconnects 402, 404 including bypass regions 406-a, 406-b having a conformation similar to shown in FIG. 4C. FIG. 5C shows another example apparatus including multiple intersection structures 508 having a closed-form curve conformation. As a non-limiting example, the example intersection structures 508 of FIG. 5C can be used with stretchable interconnects 402, 404 including bypass regions 406-a, 406-b having a conformation similar to shown in FIG. 4A or 4B.

As shown in the various conformations of stretchable interconnects of FIGS. 3A-5C, a longitudinal axis of one of the stretchable interconnects in the example apparatus may not be parallel to a longitudinal axis of another of the stretchable interconnects in the example apparatus.

In any of the example apparatus described herein, including in connection with any of FIGS. 3B-5C, the encapsulant can serve as a flexible substrate for the stretchable interconnects, including the bypass regions, and the intersection structures of the example apparatus.

The curved conformation of the intersection structure can be configured to have a radius approximately equal to the amplitude of the stretchable interconnects. As shown in FIG. 3B, the intersection structure can be configured as three layers of a material with elastic properties in the stacking structure of the intersection region.

According to the principles described herein, an example apparatus can include device components disposed on the flexible substrate and in electrical communication with the stretchable interconnects. The device components can be included in any of the example apparatus described herein, including in connection with any of FIGS. 3A-5C. The encapsulant can serve as a flexible substrate for the device components, the stretchable interconnects, including the bypass regions, and the intersection structures of the example apparatus. In the various examples, the device components can be one or more passive electronic components and/or active electronic components. Non-limiting examples of applicable device components according to the principles described herein include a transistor, an amplifier, a photodetector, a photodiode array, a display, a light-emitting device (LED), a photovoltaic device, a sensor, a semiconductor laser array, an optical imaging system, a large-area electronic device, a logic gate array, a microprocessor, an integrated circuit, an electronic device, an optical device, an opto-electronic device, a mechanical device, a microelectromechanical device, a nanoelectromechanical device, a microfluidic device, a thermal device, or other device structures.

Figure 6B:
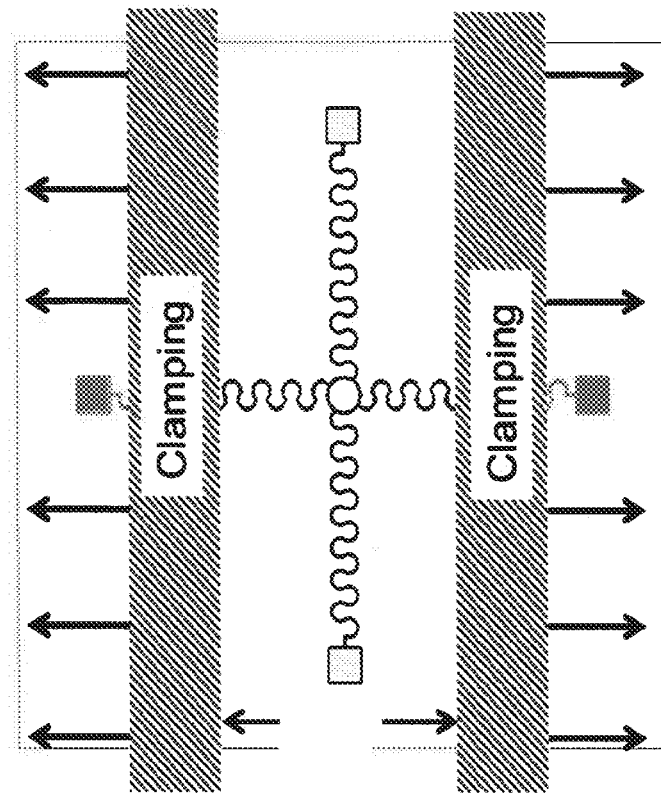
FIGS. 6A-6B show an example measurement of the elongation of an example apparatus, according to the principles described herein.
Figure 6A:
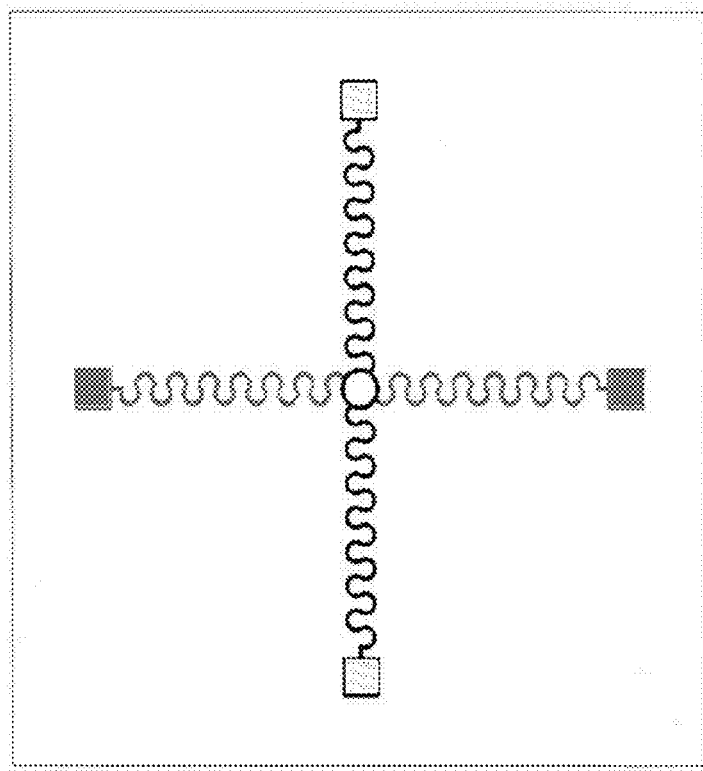

FIGS. 6A-6B show an example measurement of the elongation capabilities of an example apparatus that includes an intersection region according to the principles described herein. The example measurements demonstrate the strain tolerated by the example apparatus including the strain relief (intersection) structure. FIG. 6A shows the example apparatus that is measured. FIG. B shows the measurement setup. A strain rate of 0.5% per second is applied for the measurements. Samples are clamped as shown in FIG. 6B, and are elongated. The electrical resistance is monitored as the example apparatus is stretched. Increases in the electrical resistance are primarily due to micro-crack formation in the stretchable interconnects. As micro-cracks open and propagate, the cross-sectional area of the stretchable interconnect decreases, resulting in an increase in electrical resistance.

Figure 7A:
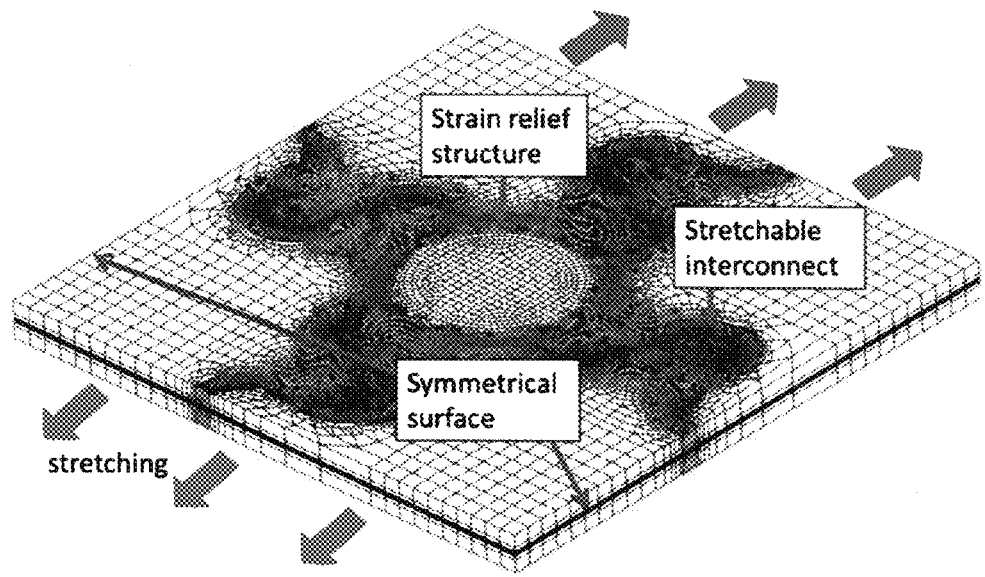
FIG. 7A-7B show a finite element model of a strain relief structure (7A) in a relaxed state and (7B) when stretched for 50% elongation, according to the principles described herein.
Figure 7B:
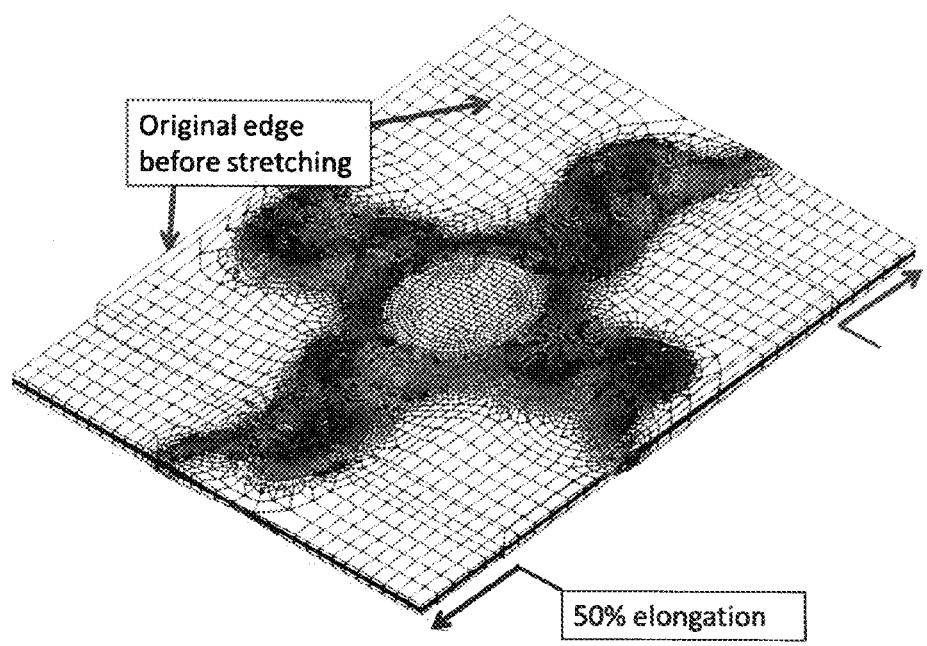

The deformation behavior of the strain relief (intersection) structure is demonstrated. FIG. 7A shows a finite element model of the strain relief (intersection) structure in a relaxed state (i.e., non-stretched). FIG. 7B shows a finite element model of the strain relief (intersection) structure when stretched for 50% elongation at two opposite ends. In this example apparatus, the strain relief (intersection) structure and stretchable interconnects are fully embedded between the flexible substrate layers (acting as an encapsulant).

Figures 8A, 8B:
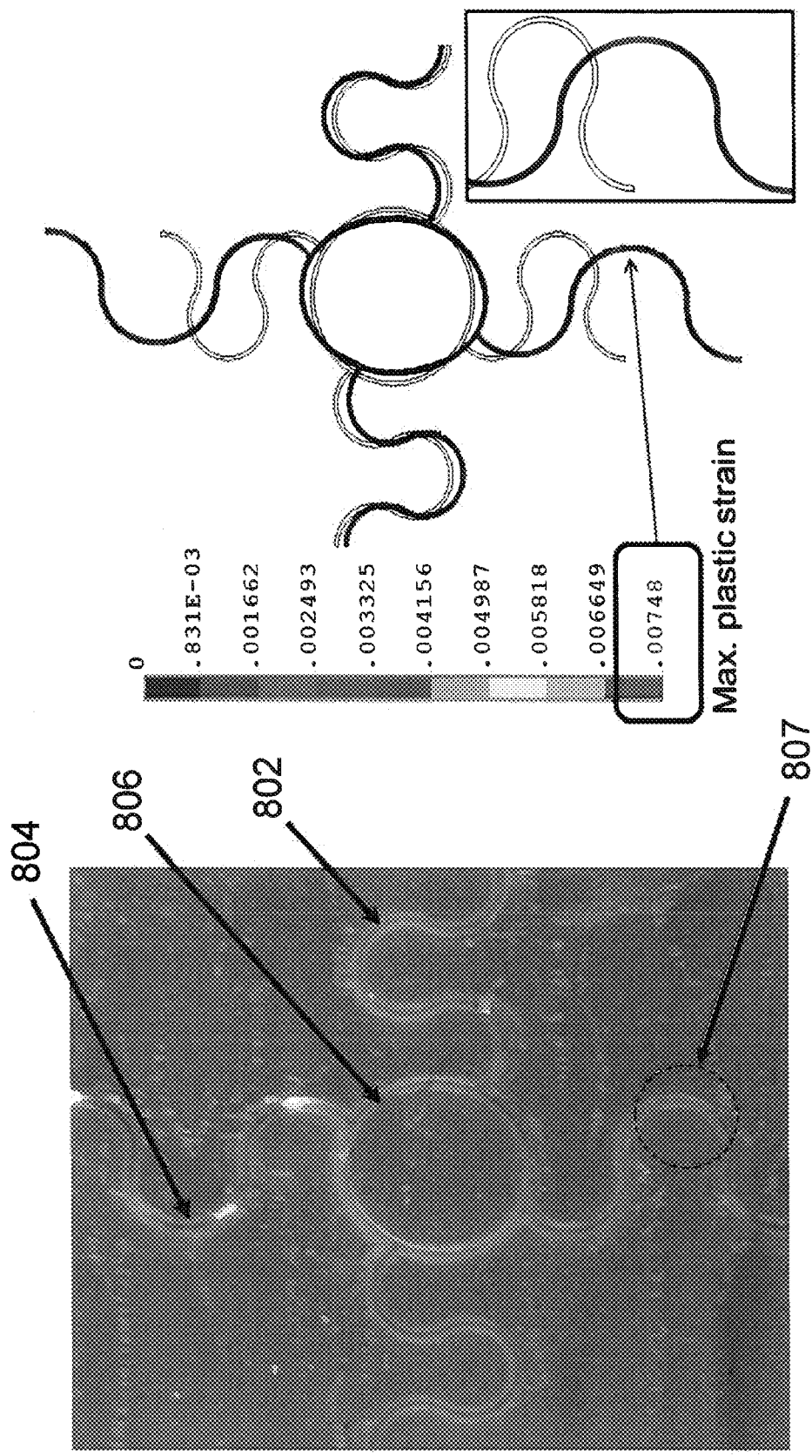
FIG. 8A shows an optical image at 50% elongation of an example apparatus, according to the principles described herein.
FIG. 8B shows the plastic strain distribution in the strain relief structure of FIG. 8A, according to the principles described herein

FIG. 8A shows an optical image at 50% elongation of an example apparatus including stretchable interconnects 802, 804 and an intersection region that include the bypass regions and the strain relief (intersection) structure 806. FIG. 8B shows the corresponding plastic strain distribution in the strain relief (intersection) structure. Both the original edge and the deformed structure are shown in FIG. 8B. The inset of FIG. 8B indicates that the plastic strain in the structure concentrates on the crest 807 of the stretch-direction horseshoe portion of the stretchable interconnect rather than at the junction of the strain relief (intersection) structure 806, indicating that the strain relief (intersection) structure effectively redistributes the plastic strain from the stretchable interconnect junctions and reduces the complexity on the mechanics at the junction. In addition, FIG. 8B shows that, as the strain relief (intersection) structure 806 is stretched, the circular structure narrows into an ellipse due to tension from the stretch-direction interconnects and the Poisson's ratio of the elastomeric substrate.

Figure 9A:
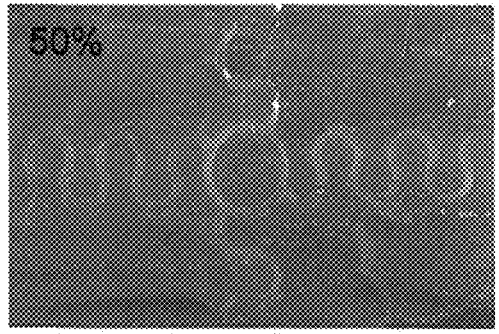
FIGS. 9A-9E show optical images of the example apparatus of FIG. 8A, as it is subjected to a progression of stretching at 50% (FIG. 9A), 100% (FIG. 9B), 150% (FIG. 9C), 200% (FIG. 9D), and 250% (FIG. 9E), according to the principles described herein.
Figure 9B:
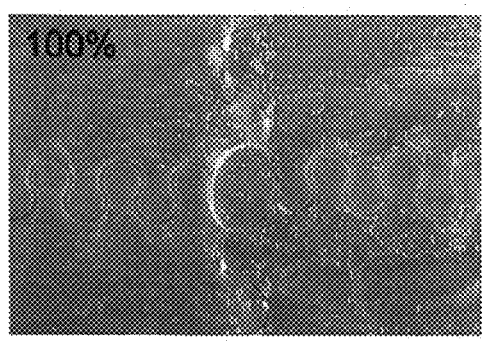
Figure 9C:
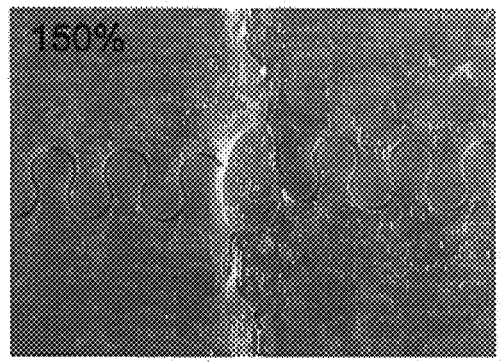
Figure 9D:
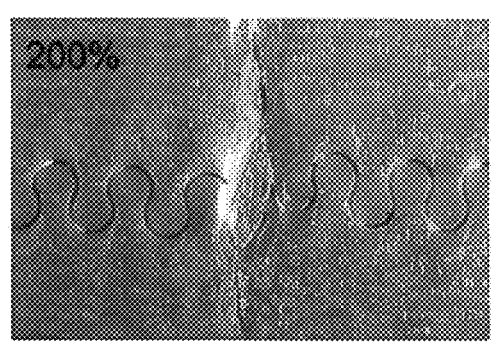
Figure 9E:
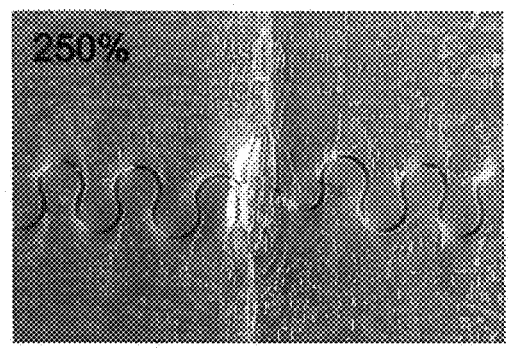

FIG. 9A-9E show optical images of the example apparatus of FIG. 8A as it is subjected to a progression of stretching at 50% (FIG. 9A), 100% (FIG. 9B), 150% (FIG. 9C), 200% (FIG. 9D), and 250% (FIG. 9E). As the strain relief (intersection) structure and stretchable interconnects are stretched from 50% to 100% strain, the strain relief (intersection) structure begins to narrow into an ellipse with its major axis along the direction of elongation as shown in FIGS. 9A and 9B, respectively. The stretchable interconnect along the direction of elongation also begins to flatten, indicating that the crest of the horseshoes of the stretchable interconnect are the regions experiencing the greatest strain. When the example apparatus is stretched to 150% elongation, as shown in FIG. 9C, the flattening of the horseshoes has increased, causing the interconnect to into a more linear shape. Also as the strain relief (intersection) structure continues to narrow into an increasingly eccentric ellipse, the strain relief (intersection) structure rotates such that the junction points of the stretch-direction interconnect also lie along the elliptical strain relief (intersection) structure's major axis. The rotation of the strain relief (intersection) structure is caused by tension in the structure at the stretch-direction junctions as the interconnect becomes almost fully elongated into a line. The junctions of the transverse interconnect also are subject to the structure's rotation. At 200% elongation, shown in FIG. 9D, the transverse interconnect junctions begin to align along the minor axis of the elliptical strain relief (intersection) structure. The stretch-direction interconnect has straightened substantially into a line with the junction point almost completely aligned by 250% elongation as shown in FIG. 9E. The transverse interconnect remains intact except for the junction points which have rotated with the strain relief (intersection) structure causing some slight flattening in the immediately adjacent horseshoes. The strain relief (intersection) structure has also elongated and narrowed to such an extent that it now has sharp, angular corners where the stretch-direction interconnect junctions are pulling on the strain relief (intersection) structure.

Figure 10:
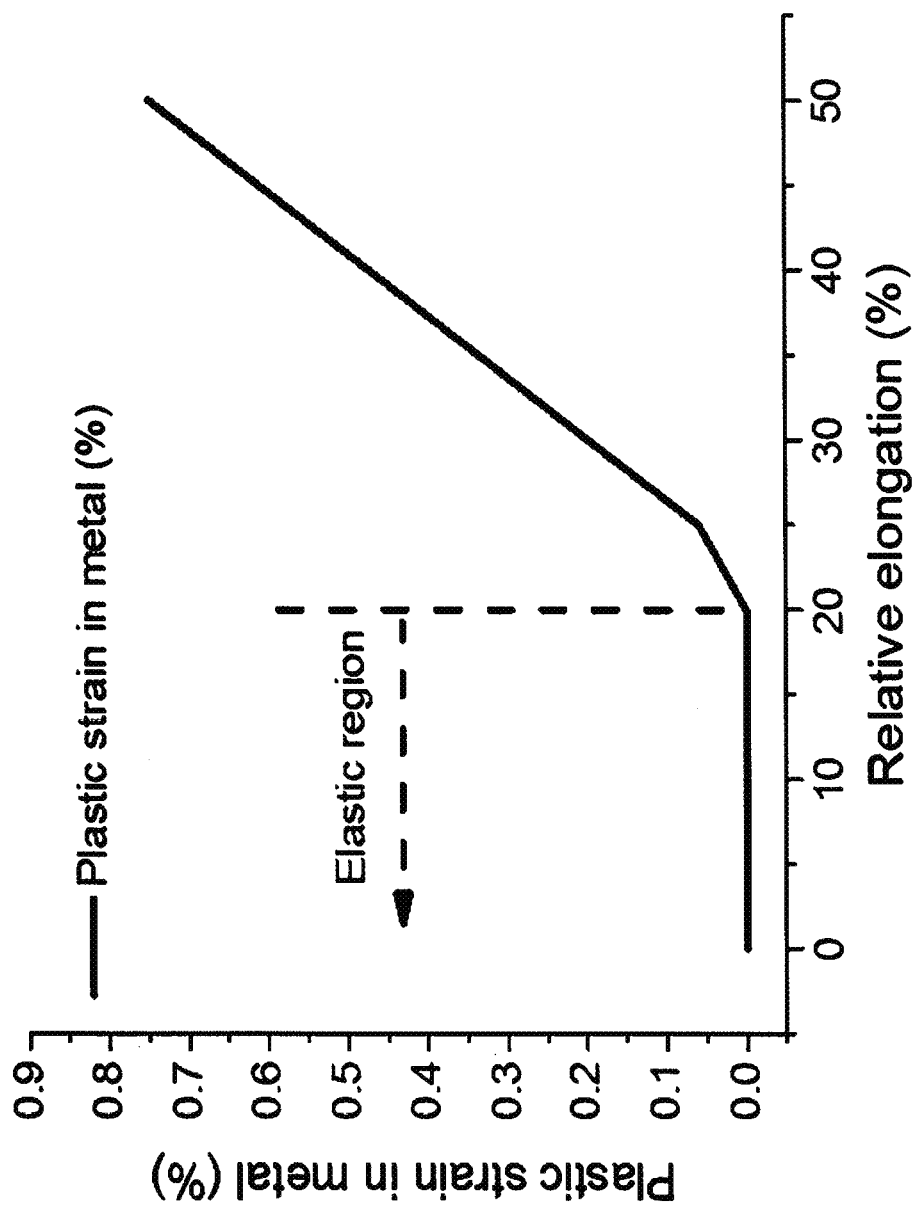
FIG. 10 shows the equivalent plastic strain in an example stretchable interconnect, according to the principles described herein.

FIG. 10 shows the maximum equivalent plastic strain in the stretchable interconnect as a function of the relative elongation of the substrate. The curve indicates that the maximum plastic strain in the crest of the horseshoes of the stretchable interconnect remains zero while the structure is stretched up to 20% elongation. A 20% elongation marks the onset of plastic strain in the structure, which begins accumulating in the stretchable interconnect at that point. Prior to this onset point, the interconnects stay within the elastic deformation region. After this onset point, the plastic strain increases nonlinearly up to 0.75% at 50% elongation. These values are well below the reported fracture strain of gold film deposited on an elastomeric substrate.

Figure 11:
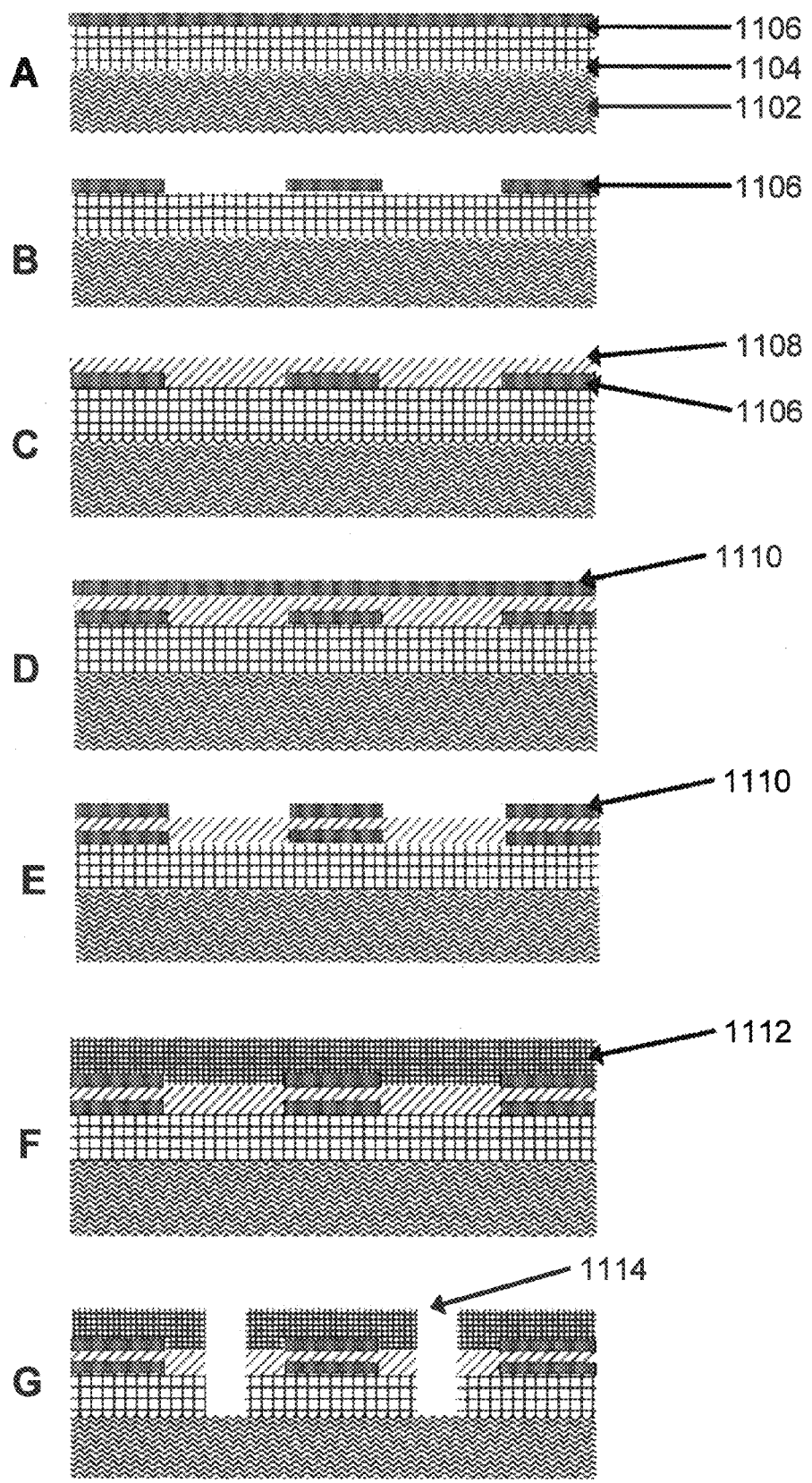
FIGS. 11A-11L show an example process flow for fabrication of an example apparatus or an example device, according to the principles described herein.
Figure 11:
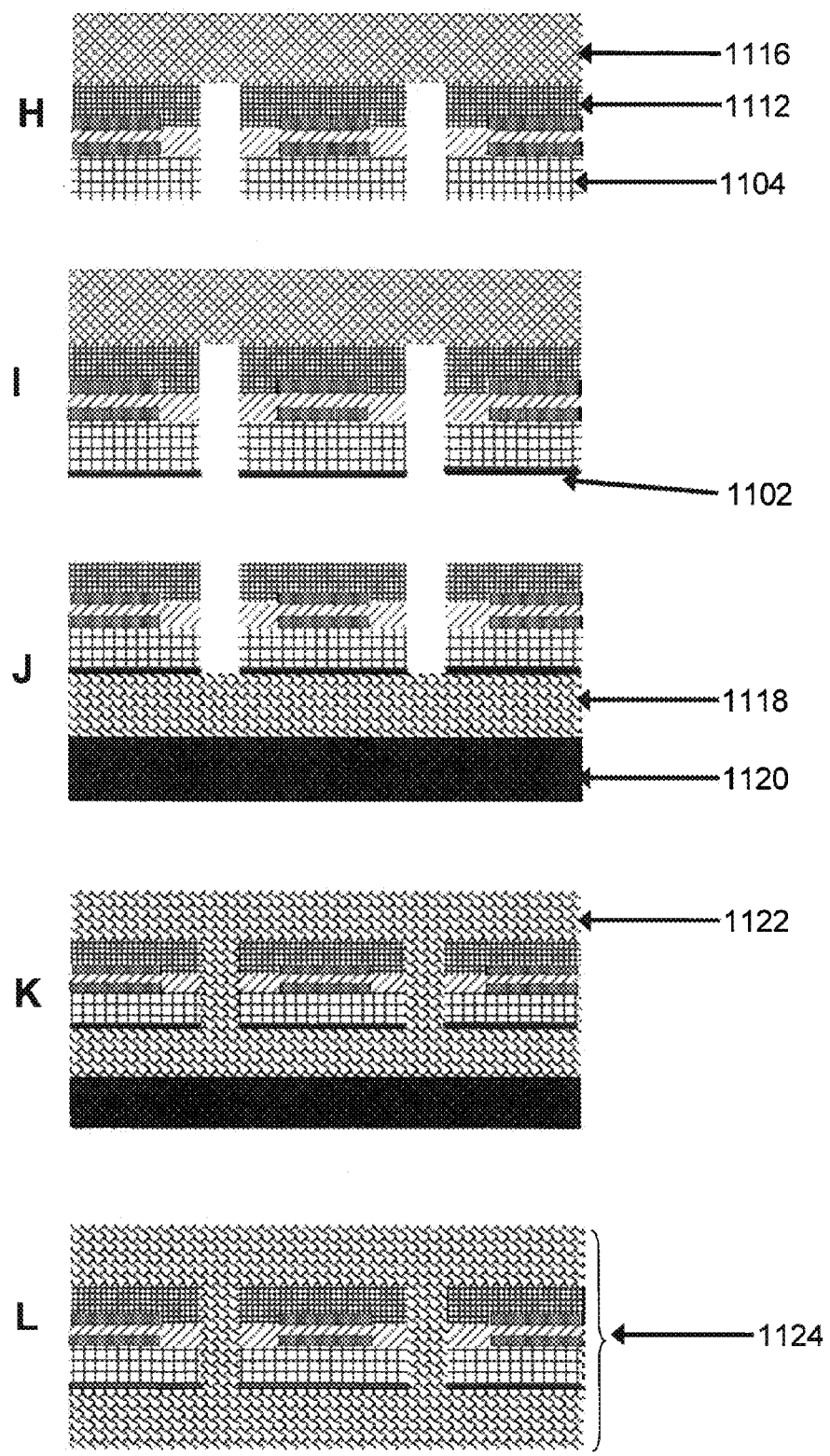

FIGS. 11A-11L show a non-limiting example process flow for fabrication of an example apparatus or an example device according to the principles described herein. FIG. 11A shows a layer structure that includes a base wafer 1102, a base polymer layer 1104, and a conductive film 1106. The wafer 1102 can be a silicon wafer. The polymer 1104 can be a polyimide. The conductive film 1106 can be a gold layer. In FIG. 11B, the conductive film 1106 is patterned. The patterning provides the features of a stretchable interconnect including a bypass region. In FIG. 11C, a polymer layer 1108 is spin-coated or laminated over the patterned conductive layer 1106. In FIG. 11D, a second layer of conductive material 1110 is deposited. In FIG. 11E, the second layer of conductive material 1110 is patterned to provide the features of a second stretchable interconnect including its respective bypass region. A polymer layer 1112 is spin-coated or laminated in FIG. 11F, and channels 1114 are etched through the fabricated layers to the base wafer in FIG. 11G. In FIG. 11H, a temporary tape 1116 is used to transfer the fabricated layers for further processing. A dielectric layer is deposited in FIG. 11I. In an example, the dielectric layer is $SiO_2$. The dielectric is plasma treated to functionalize the surface, and in FIG. 11J the structure is bonded to a polymer coating 1118 on a second substrate 1120. In FIG. 11K, the structure is spin-coated with a polymer 1122. In FIG. 11L, the structure is encapsulated with an encapsulant. An example apparatus 1124 according to the principles described herein is obtained.

An example implementation of the process of FIGS. 11A-11L is described for the fabrication of an example apparatus. A polyimide layer (DURIMIDE 7000®, Fujifilm, Mesa Ariz.) was spun onto a "source" silicon wafer, followed by 0.5 μm thick deposition of a gold (Au) film. The Au film is patterned using photolithography and chemical etching to form the first layer of the stretchable interconnect and the bypass region that forms the circular strain relief (intersection) structure. A second polyimide layer is spun onto the structure to form a 2 μm thick intermediate layer, followed by a second layer 0.5 μm thick layer of gold film. This second metal layer followed the similar patterning as the first metal layer. In patterning the second metal layer, the horseshoe-patterned stretchable interconnect is oriented perpendicularly to the first interconnect, while the second layer of the bypass region that forms the strain relief (intersection) structure is aligned with that of the first layer. To embed the multi-layer interconnects, another polyimide layer is spin-coated on top of the patterned structure. A layer of $SiO_2$ is deposited and patterned. The polyimide not covered by the $SiO_2$ is etched away by means of reactive ion etching. A temporary transfer tape is used to release the structure from the source wafer, and $SiO_2$ is deposited onto the back side of the structure as well as that of the transfer tape. ECOFLEX® (Smooth-On Inc., Easton Pa.) is spun on a Teflon coated "target" wafer to form a 0.2 μm thick layer of elastomer on the target wafer. The strain relief (intersection) structure, stretchable interconnects and the elastomer are treated with $O_2$ plasma to allow the two surfaces to bond. A 0.2 μm thick layer of ECOFLEX® is deposited onto the structures. FIG. 3A shows the example apparatus including the strain relief (intersection) structure and stretchable interconnects.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention may be implemented in any of numerous ways. For example, some embodiments may be implemented using hardware, software or a combination thereof. When any aspect of an embodiment is implemented at least in part in software, the software code may be executed on any suitable processor or collection of processors, whether provided in a single device or computer or distributed among multiple devices/computers.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc

What is claimed is:

1. An apparatus comprising:
   a first conductive stretchable interconnect having a first portion electrically coupled to a second portion via a first bypass portion, the first bypass portion having a curved shape, the first conductive stretchable interconnect being positioned in a first layer of the apparatus;
   a second conductive stretchable interconnect having a first portion electrically coupled to a second portion via a second bypass portion, the second bypass portion, having a curved shape substantially the same as the curved shape of the first bypass portion, the second conductive stretchable interconnect being positioned in a second layer of the apparatus that is spaced from the first layer of the apparatus such that the first and second stretchable interconnects overlap at an intersection region of the apparatus; and
   an intersection structure having a top layer, a middle layer, and a bottom layer, the first conductive stretchable interconnect being positioned between the top and middle layers and the second conductive stretchable interconnect being positioned between the middle and bottom layers, such that the intersection structure encompasses at least a portion of the first and second bypass portions, the intersection structure being configured to redistribute a mechanical strain on the first bypass portion and the second bypass portion away from the intersection region of the apparatus.

2. The apparatus of claim 1, wherein the intersection structure is formed from a polymer.

3. The apparatus of claim 2 wherein the polymer is a polyimide.

4. The apparatus of claim 1, wherein the first conductive stretchable interconnect or the second conductive stretchable interconnect comprises gold, copper, aluminum, stainless steel, silver, a doped semiconductor, a conductive polymer, or any combination thereof.

5. The apparatus of claim 1, further comprising an encapsulant that encapsulates the first conductive stretchable interconnect and the second conductive stretchable interconnect.

6. The apparatus of claim 5, wherein the encapsulant is an elastomer.

7. The apparatus of claim 1, wherein each of the top, middle, and bottom layers of the intersection structure comprises a rounded segment.

8. The apparatus of claim 1, wherein the intersection structure comprises at least one closed curve portion.

9. The apparatus of claim 1, wherein a longitudinal axis of the first conductive stretchable interconnect is not parallel to a longitudinal axis of the second conductive stretchable interconnect.

10. The apparatus of claim 1, wherein the first conductive stretchable interconnect and the second conductive stretchable interconnect has a zig-zag conformation, a serpentine configuration, or a rippled configuration.

11. The apparatus of claim 1, wherein a first central axis of the first bypass portion is concentric with a second central axis of the second bypass portion.

12. The apparatus of claim 1, wherein the curved shape of the first bypass portion is a closed curved shape and wherein the curved shape of the second bypass portion is a closed curved shape.

13. A device comprising:
a flexible substrate
at least two device components disposed over the flexible substrate;
a first conductive stretchable interconnect in electrical communication with at least one of the at least two device components, the first conductive stretchable interconnect having a first portion electrically coupled to a second portion via a first bypass portion, the first bypass portion having a closed curved shape, the first conductive stretchable interconnect being positioned in a first layer of the apparatus;
a second conductive stretchable interconnect in electrical communication with at least one other of the at least two device components, the second conductive stretchable interconnect having a first portion electrically coupled to a second portion via a second bypass portion, the second bypass portion having a closed curved shape substantially the same as the curved shape of the first bypass portion, the second conductive stretchable interconnect being positioned in a second layer of the apparatus that is spaced from the first layer of the apparatus such that the first and second stretchable interconnects overlap at an intersection region of the apparatus; and
an intersection structure having a top layer, middle layer, and a bottom layer, the first conductive stretchable interconnect being positioned between the top and middle layers and the second conductive stretchable interconnect being positioned encompasses at least a portion of the first and second bypass portions, the intersection structure being configured to redistribute a mechanical strain on the first bypass portion and the second bypass portion away from the intersection region of the apparatus.

14. The device of claim 13, wherein at least one of the at least two device components is an electronic device, an optical device, an opto-electronic device, a mechanical device, a microelectromechanical device, a nanoelectromechanical device, a microfluidic device and a thermal device.

15. The device of claim 13, wherein the intersection structure is formed from a polymer.

16. The device of claim 15, wherein the polymer is a polyimide or an elastomer.

17. The device of claim 13, wherein the first conductive stretchable interconnect or the second conductive stretchable interconnect comprises gold, copper, aluminum, stainless steel, silver, a doped semiconductor, a conductive polymer, or any combination thereof.

18. The device of claim 13, furter comprising an encapsulant that encapsulates the at least two device components, the first stretchable interconnect, and the second stretchable interconnect.

19. The device of claim 18, wherein the encapsulant is an elastomer.

20. The device of claim 13, wherein each of the top, middle, and bottom layers of the intersection structure comprises a rounded segment.

21. The device of claim 13, wherein the intersection structure comprises at least one closed curve portion.

22. The device of claim 13, wherein a longitudinal axis of the first conductive stretchable interconnect is not parallel to a longitudinal axis of the second conductive stretchable interconnect.

23. The device of claim 13, wherein the first conductive stretchable interconnect and the second conductive stretchable interconnect has a zig-zag conformation, a serpentine configuration, or a rippled configuration.

24. The apparatus of claim 13, wherein a first central axis of the first bypass portion is concentric with a second central axis of the second bypass portion.

25. An apparatus comprising:
a first conductive stretchable interconnect including a first bypass portion having a first central axis, the first conductive stretchable interconnect being positioned in a first layer of the apparatus;
a second conductive stretchable interconnect having a second bypass portion having a second central axis, the second conductive stretchable interconnect being positioned in a second layer of the apparatus that is spaced from the first layer of the apparatus such the second central axis is coincident with the first central axis and the first and second stretchable interconnects intersect at an intersection region of the apparatus; and
an intersection structure encompassing at least a portion of the first and second bypass portions and being configured to redistribute a mechanical strain on the first bypass region and the second bypass region away from the intersection region of the apparatus.

26. The apparatus of claim 25, wherein the first bypass portion has a closed curved shape and the second bypass portion has a closed curved shape that is substantially the same as the closed curved shape of the first bypass portion.

27. The apparatus of claim 25, wherein the intersection structure has a closed curved shape.

28. The apparatus of claim 25, wherein the first conductive stretchable interconnect further included a first portion electrically coupled to a second portion via the first bypass portion and the second conductive stretchable interconnect further includes a first portion electrically coupled to a second portion via the second bypass portion.

29. The apparatus of claim 25, wherein the intersection structure includes a top layer, a middle layer, and a bottom layer, and wherein the first conductive stretchable interconnect is positioned between the top and middle layers and the second conductive stretchable interconnect is positioned between the middle and bottom layers.

30. The apparatus of claim 29, wherein each of the top, middle, and bottom layers of the intersection structure has a substantially similar closed curved shape.

* * * * *

UNITED STATES PATENT AND TRADEMARK OFFICE
CERTIFICATE OF CORRECTION

| | | |
|---|---|---|
| PATENT NO. | : 9,247,637 B2 | Page 1 of 1 |
| APPLICATION NO. | : 13/843880 | |
| DATED | : January 26, 2016 | |
| INVENTOR(S) | : Yung-Yu Hsu | |

It is certified that error appears in the above-identified patent and that said Letters Patent is hereby corrected as shown below:

In the claims,

In Column 16, Line 1, in Claim 18, please replace "The device of claim 13, furter comprising" with --The device of claim 13, further comprising--.

Signed and Sealed this
Nineteenth Day of April, 2016

Michelle K. Lee
*Director of the United States Patent and Trademark Office*